(12) United States Patent
Hedberg et al.

(10) Patent No.: US 8,781,580 B2
(45) Date of Patent: Jul. 15, 2014

(54) PACING SEQUENCE OPTIMIZATION

(71) Applicant: St. Jude Medical AB, Jarfalla (SE)

(72) Inventors: Sven-Erik Hedberg, Kungsangen (SE); Malin Hollmark, Solna (SE); Stefan Hjelm, Balsta (SE); Michael Broome, Ekero (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/648,984

(22) Filed: Oct. 10, 2012

(65) Prior Publication Data

US 2013/0289642 A1    Oct. 31, 2013

Related U.S. Application Data

(60) Provisional application No. 61/554,026, filed on Nov. 1, 2011.

(30) Foreign Application Priority Data

Oct. 24, 2011    (EP) ..................................... 11186404

(51) Int. Cl.
*A61N 1/18* (2006.01)
*A61N 1/362* (2006.01)
*A61N 1/365* (2006.01)

(52) U.S. Cl.
CPC .............. *A61N 1/365* (2013.01); *A61N 1/36514* (2013.01); *A61N 1/36585* (2013.01); *A61N 1/3627* (2013.01); *A61N 1/36507* (2013.01)
USPC ........................................................... 607/9

(58) Field of Classification Search
None
See application file for complete search history.

(56) References Cited

U.S. PATENT DOCUMENTS

| 5,514,163 | A  | 5/1996  | Markowitz et al. |
| 6,044,299 | A  | 3/2000  | Nilsson |
| 6,522,923 | B1 | 2/2003  | Turcott |
| 6,751,504 | B2 | 6/2004  | Fishler |
| 6,804,555 | B2 | 10/2004 | Warkentin |
| 7,123,962 | B2 | 10/2006 | Siejko et al. |
| 7,209,786 | B2 | 4/2007  | Brockway et al. |
| 7,418,868 | B1 | 9/2008  | Karicherla et al. |

(Continued)

FOREIGN PATENT DOCUMENTS

| WO | 2005107583 A2 | 11/2005 |
| WO | 2005107583 A3 | 12/2006 |
| WO | 2011069538 A1 | 6/2011 |

OTHER PUBLICATIONS

European Search Report, dated Dec. 23, 2011—EP App. No. 11186404.7.

(Continued)

*Primary Examiner* — Brian T Gedeon

(57) ABSTRACT

An implantable medical device is connected to a multipolar LV lead and an implantable sensor. The sensor signal from the sensor is used to identify a time point of mitral valve closure for a cardiac cycle when a ventricular pulse generator generates pacing pulses that are applied to the electrodes of the multipolar LV lead according to a pacing sequence. A time interval processor determines the time interval from onset of LV activation to the time point of mitral valve closure. This procedure is repeated for multiple different pacing sequences of a sequence set. The pacing sequence that resulted in shortest time interval is then selected by a selector as the currently optimal pacing sequence for the patient.

15 Claims, 6 Drawing Sheets

(56) References Cited

U.S. PATENT DOCUMENTS

| | | | |
|---|---|---|---|
| 7,515,971 | B1 | 4/2009 | Doan |
| 7,689,283 | B1 | 3/2010 | Schecter |
| 7,848,807 | B2 | 12/2010 | Wang |
| 8,112,150 | B2 * | 2/2012 | Naqvi et al. ............ 607/5 |
| 2002/0151938 | A1 | 10/2002 | Corbucci |
| 2003/0199936 | A1 | 10/2003 | Struble et al. |
| 2008/0004667 | A1 * | 1/2008 | Arcot-Krishnamurthy et al. ............ 607/17 |
| 2012/0296228 | A1 * | 11/2012 | Zhang et al. ............ 600/513 |

OTHER PUBLICATIONS

Braunwald, Eugene MD, "Mitral Regurgitation—Physiologic, Clinical and Surgical Consideration," N Engl J of Medicine. Aug. 21, 1969;281:425-433.

Burch, G.E. MD et al., "The syndrome of papillary muscle dysfunction," Am Heart J. Mar. 1968;75(3):399-415.

Cheng, Tsung O. MD, MS (Med), "Some New Observations on the Syndrome of Papillary Muscle Dysfunction," Am J Medicine. Dec. 1969;47:924-945.

De Busk, Robert F. MD et al., "The Clinical Spectrum of Papillary-Muscle Disease," N Eng J of Medicine. Dec. 25, 1969; 281:1458-1467.

Levine, Robert A. et al., "Ischemic Mitral Regurgitation on the Threshold of a Solution: From Paradoxes to Unifying Concenpts," Circulation. 2005;112:745-758.

Schlant, Robert C. MD, "The Management of Chronic Mitral Regurgitation," American Heart Association—Council on Clinical Cardiology. Mar. 1986;12(1): 10 pages.

Zuber, Michel MD et al., "A Comparison of Acoustic Cardiography and Echocardiography for Optimizing Pacemaker Settings in Cardiac Resynchronization Therapy," PACE. Jul. 2008;31:802-811.

Zuber, Michel et al., "Comparison of different approaches for optimization of atrioventricular and interventricular delay in biventricular pacing," Europace. Mar. 2008;10(3):367-373.

Nof, Eyal MD et al., "Mechanism of Diastolic Mitral Regurgitation in Candidates for Cardiac Resynchronization Therapy," Am J Cardiol. Jun. 1, 2006;97(11):1611-1614.

"Optimizing Cardiac Resynchronization Therapy Using Acoustic Cardiography and AV/VV Delay Maps," Heart Failure: Resynchronization Therapy III Meeting. Circulation Supplement. Oct. 16, 2007;116(16): Abstract 3282.

* cited by examiner

PACING SEQUENCE OPTIMIZATION

CROSS REFERENCE TO RELATED APPLICATIONS

This application claims the benefit of U.S. Provisional Patent Application Ser. No. 61/554,026, filed Nov. 1, 2011, titled "Pacing Sequence Optimization," and European Patent Application No. 11186404.7, filed Oct. 24, 2011.

TECHNICAL FIELD

The embodiments generally relate to cardiac pacing and in particular to selection of optimal pacing sequence for an implantable medical device connectable to a multipolar lead.

BACKGROUND

The conventional approach in cardiac resynchronization therapy (CRT) involves pacing from an electrode provided close to the right ventricular (RV) apex, an electrode on a transvenous left ventricular (LV) lead, typically in the lateral or postero-lateral vein, and optionally an electrode in the right atrium (RA).

In such a case, the optimal interventricular (VV) delay between RV and LV pacing pulses and the optimal atrioventricular (AV) delay between atrial and ventricular pacing need to be determined. Several prior art solutions to such optimization problems have been suggested. U.S. Pat. No. 5,514,163 optimizes an AV delay based on far field R wave sense (FFRS) duration. U.S. Pat. Nos. 6,751,504; 6,804,555 use the width of the QRS in order to set optimal VV delays. In another document, U.S. Pat. No. 7,848,807, optimal AV and VV delays are determined based on the width of a P wave from a sensed far-field electrocardiogram.

A problem with the prior art CRT is that several heart failure patients do not respond well to the selected biventricular CRT. Thus, there is a need for a CRT that is capable of achieving physiologically suitable heart contraction and thereby lead to improvements also for the non-responding heart failure patient.

U.S. Pat. No. 6,522,923 is directed towards finding optimal AV and VV delays by testing a set of randomly selected AV and VV delays within a defined AV/VV space. The most optimal of the tested AV and VV combinations is found and a new set of randomly selected AV and VV delays are tested within a smaller AV/VV space centered at the most optimal AV/VV-combination. This procedure is repeated multiple times with ever smaller AV/VV spaces until a final optimal combination of AV and VV delays is found.

Zuber et al., *Pace* 2008, 31: 802-811 discloses a comparison of acoustic cardiography and echocardiography for optimizing pacemaker settings in CRT. It was concluded that for CRT optimization acoustic cardiography provides results similar to echocardiography but with improved reproducibility and ease of use.

Zuber et al., *Europace* 2008, 10: 367-373 discloses a comparison of different approaches for optimization of AV and VV delay in biventricular pacing. The authors conclude that it is advisable to measure a full grid of AV and VV delays to identify optimal settings rather than optimizing one of the two delays first.

There is, however, still a need for efficient techniques to determine optimal pacing sequence for an implantable medical device having a multipolar cardiac lead.

SUMMARY

An aspect of the embodiments defines an implantable medical device (IMD) comprising a connector that is connectable to a multipolar left ventricular (LV) lead having multiple pacing electrodes configured to be arranged at multiple respective sites in connection with a patient's left cardiac ventricle. The connector is also connectable to an implantable sensor configured to generate a sensor signal recorded from the heart. Alternatively, the implantable sensor is comprised within the implantable medical device. A ventricular pulse generator is configured to generate pacing pulses to be applied to the multiple electrodes of the multipolar LV lead. The ventricular pulse generator is controlled by a pulse generator controller that controls the ventricular pulse generator to generate pacing pulses according to multiple different pacing sequences of a sequence set. Each such pacing sequence defines a pacing order at which pacing pulses are applied to the multiple electrodes of the multipolar LV lead and pulse-to-pulse delays of applying these pacing pulses to the multiple electrodes. An activation detector is connected to the connector and configured to detect onset of activation of the left ventricle for a cardiac signal. A valve closure processor of the IMD is configured to process the sensor signal from the implantable sensor to determine a respective time point of closure of the mitral valve following application of pacing pulses according to the different pacing sequences. A time interval processor determines a time interval for each pacing sequence corresponding to the time from onset of LV activation to the time point of closure of the mitral valve for a cardiac cycle during which the left ventricle is paced according to the particular pacing sequence. The IMD also comprises a selector configured to select the pacing sequence of the sequence set that resulted in the shortest time interval as determined by the time interval processor. Information of this selected pacing sequence is stored in a memory of the IMD to thereby enable identification of the selected pacing sequence as the currently optimal pacing sequence for the patient.

Another aspect of the embodiments relates to a method of selecting a pacing sequence for an IMD. The method comprises applying pacing pulses to the multiple electrodes of a multipolar LV lead according to multiple different pacing sequences of a sequence set. Onset of activation of the left ventricle is determined for each application of pacing pulses. A respective time point of closure of the mitral valve of the heart is determined for at least one respective cardiac cycle during which the heart is paced according to the respective pacing sequences of the sequence set. A respective time interval from onset of LV activation until the time point of closure of the mitral valve is determined for each pacing sequence of the sequence set. The pacing sequence resulting in the shortest time interval is then selected and identified as the currently optimal pacing sequence for the patient.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The embodiments generally relate to cardiac pacing and in particular to selection of optimal pacing sequence for an implantable medical device connectable to a multipolar lead. Thus, the present embodiments utilize a multipolar lead, preferably a multipolar left ventricular (LV) lead having multiple pacing electrodes to be arranged in connection with a left ventricle of a subject's heart. The embodiments determine an optimal pacing sequence defining the order at which pacing pulses are applied to these multiple pacing electrodes and the pulse-to-pulse delays between the application of the pacing pulses to the multiple electrodes.

The present embodiments can thereby obtain a pacing sequence or pattern that mimics the natural activation and contraction sequence in the left ventricle while minimizing mitral regurgitation, shortening the isovolumic preejection phase and resulting in an efficient ejection phase of the heart.

Figure 1:
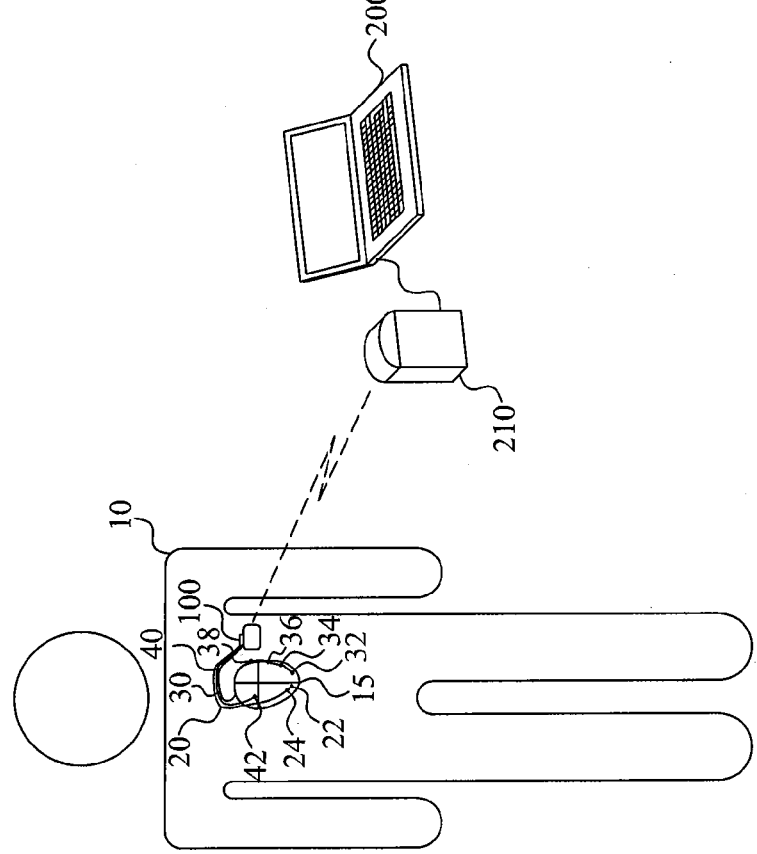
FIG. 1 is an overview of a human subject having an implantable medical device according to an embodiment.

FIG. 1 is a schematic overview of a subject, represented by a human subject 10 having an implantable medical device (IMD) 100 according to the embodiments. The IMD 100 is implanted in the subject 10 in order to provide pacing therapy to the subject's heart 15. The IMD 100 can be in the form of a pacemaker or an implantable cardioverter-defibrillator (ICD). The IMD 100 is, during operation in the subject's body, connected to a multipolar LV lead 30 having multiple pacing electrodes 32, 34, 36, 38. As is well known in the art, a multipolar LV lead 30 is provided on the outside of the heart 15 typically in the coronary venous system, e.g. in a left lateral vein or a postero-lateral vein. The multipolar LV lead 30 enables the IMD 100 to apply pacing pulses to the left ventricle and sense electrical activity from the left ventricle. The IMD 100 can also be connected to other cardiac leads, for instance a right ventricular (RV) lead 20 and/or an atrial lead 40. An RV lead 20 is typically provided inside the right ventricle of the heart 15 and comprises one or more electrodes 22, 24 that can be used by the IMD 100 to apply pacing pulses to the right ventricle and/or sense electrical activity from the right ventricle. An atrial lead 40, typically a right atrial (RA) lead 40 having at least one electrode 42 arranged in or in connection with the right atrium, can be used by the IMD 100 in order to provide atrial pacing and/or sensing. Instead of or as a complement to an RA lead, the IMD 100 can be connected to a left atrial (LA) lead.

FIG. 1 additionally illustrates a non-implantable data processing device 200, such as in the form of a programmer, a home monitoring device or a physician's workstation. The data processing device 200 comprises or is connected to a communication module or device 210 that is capable of wirelessly communicating with the IMD 100, preferably through radio frequency (RF) based communication or inductive telemetry. The data processing device 200 can then use the communication module 210 in order to interrogate the IMD 100 for diagnostic data recorded by the IMD 100 employing the electrodes 22, 24, 32, 34, 36, 38, 42 of the connected cardiac lead(s) 20, 30, 40. Furthermore, the data processing device 200 can be used to program the IMD 100, such as by setting one or more programmable CRT parameters. According to the present embodiments, the data processing device 200 can in particular be used in order to define a sequence set of multiple different pacing sequences to be tested by the IMD 100.

The communication module 210 and the data processing device 200 can be separate devices as illustrated in FIG. 1, either wired connected or using a wireless connection, such as Bluetooth®, an infrared (IR) connection or an RF connection. In an alternative embodiment, the functionality and equipment of the communication module 210 can be housed within the data processing device 200.

The present embodiments perform an optimization of the pacing sequence or pattern applied through the multipolar LV lead 30 based on a particular optimization criterion. This optimization criterion is the time point of the onset of activation of the left ventricle until closure of the mitral valve of the heart 15. Thus, the pacing sequence that minimizes the time interval from onset of LV activation until the mitral valve closure is identified and used as currently optimal pacing sequence for the IMD 100.

Figure 2:
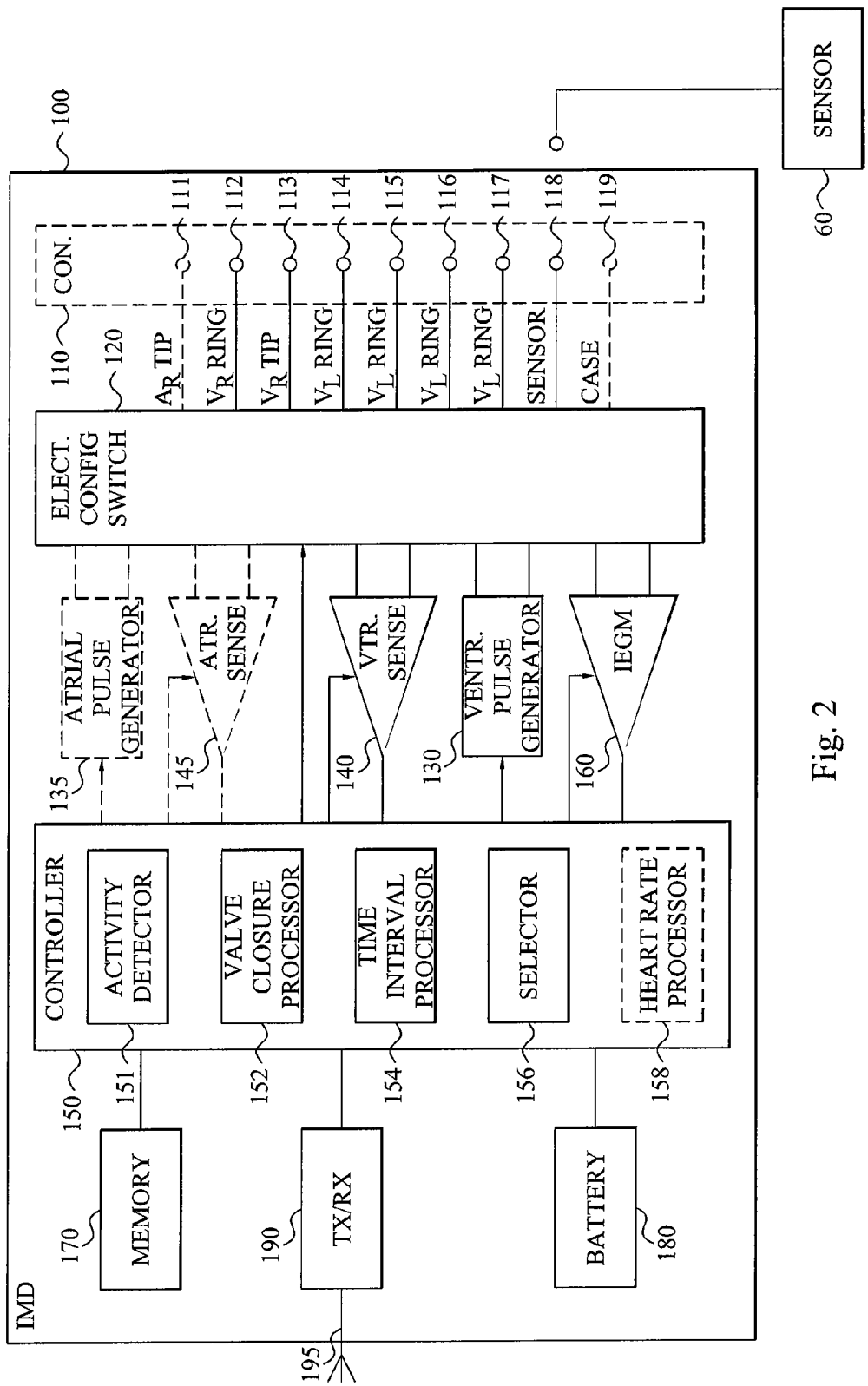
FIG. 2 is a schematic block diagram of an implantable medical device according to an embodiment.

FIG. 2 is a schematic block diagram of an embodiment of an IMD 100 according to the embodiments. The IMD 100 comprises a connector 110 having connector terminals 111-117 configured to be connected to matching electrode terminals of one or more cardiac leads. In particular, the connector 110 is connectable to a multipolar LV lead 30 as previously described herein. Thus, the connector 110 comprises multiple connector terminals 114-117, each of which is electrically connectable to a respective electrode terminal of the multipolar LV lead 30. The multipolar LV lead 30 of the embodiments comprises N pacing electrodes configured to be arranged at multiple respective sites in connection with the left ventricle. This number N is an integer equal to or larger than three. Thus, N could be three, four, five, six or even larger. In FIG. 1 the multipolar LV lead 30 is exemplified by a quadropolar LV lead, i.e. N=4. The connector 110 therefore comprises four connector terminals 114-117 for electrical connection with the electrodes 32, 34, 36, 38 of the multipolar LV lead 30 in this implementation example.

The connector 110 may furthermore comprise at least one terminal 118 connectable to an implantable sensor 60. This implantable sensor 60 is configured to generate a sensor signal recorded for the heart and from which a time point of closure of the mitral valve of the heart can be determined for a cardiac cycle. Different implementation embodiments of the sensor 60 will be further discussed herein. In an alternative approach the implantable connector 100 does not need to be connected through the connector 110. In clear contrast, the implantable sensor 60 could constitute a part of the IMD 100 and be present within the housing or closure of the IMD 100. In such a case, the connector 110 does not need any terminal 118 that is connectable to the implantable sensor 60. In clear contrast, the implantable sensor 60 could then instead be connected to a valve closure processor 152 of the IMD 100.

The IMD 100 comprises a valve closure processor 152 connected, optionally through an electronic configuration switch 120, to the connector 110 or directly, or through the optional switch 120, to the implantable sensor 60. This valve closure processor 152 is configured to process the sensor signal from the implantable sensor 60. In more detail, the valve closure processor 152 determines a time point of closure of the mitral valve of the heart for a cardiac cycle based on the sensor signal.

The IMD 100 also comprises a ventricular pulse generator 130 connected to the connector 110, optionally through the electronic configuration switch 120. The ventricular pulse generator 130 is configured to generate pacing pulses to be applied, through the optional switch 120 and the connector 110, to multiple pacing electrodes of the multipolar LV lead.

The ventricular pulse generator 130 is connected to and controlled by a pulse generator controller, represented by a general controller 150 in FIG. 2. The controller 150 controls the particular pacing pattern to be applied to the left ventricle of the subject's heart by the multipolar LV lead and the ventricular pulse generator 130. In particular, the controller 150 is configured to control the ventricular pulse generator 130 to generate pacing pulses to be applied to the multiple pacing electrodes of the multipolar LV lead according to multiple different pacing sequences of a sequence set. This sequence set comprises multiple, i.e. at least two, different pacing sequences and where each such pacing sequence defines a pacing order at which pacing pulses are applied to the multiple pacing electrodes of the multipolar LV lead and the pulse-to-pulse delays of applying the pacing pulses according to the pacing order.

The pacing sequences in the sequence set are different from each other. Hence, a pacing sequence of the sequence set uses a different pacing order and/or different pulse-to-pulse delays as compared to the other pacing sequences of the sequence set. If the pacing order is different between different pacing sequences, the controller 150 controls the optional switch 120 to interconnect the ventricular pulse generator 130 to the correct terminals 114-117 of the connector 110 to thereby apply pacing pulses to the electrodes of the multipolar LV lead according to the defined pacing order for that particular pacing sequence. Correspondingly, controller 150 controls the ventricular pulse generator 130 to generate pacing pulses according to the time schedule, i.e. with defined pulse-to-pulse delays, according to the particular pacing sequence and/or controls the switch 120 to time the interconnections between the terminals 114-117 and the ventricular pulse generator 130 to apply the pacing pulses according to the correct pulse-to-pulse delays.

The IMD 100 further comprises an activation detector 151 that is configured to detect onset of activation of or at the left ventricle for the cardiac cycles during which the pulse generator 130 generates the pacing pulses according to the pacing sequences. The activation detector 151 could perform this onset detection based on at least one signal received by the connector 110. The signal can be an electric signal sensed from one or more of the connected electrodes or a signal from a connected sensor 60. Alternatively, the activation detector 151 detects the onset of activation based on the generation and/or application of the respective first pacing pulse per pacing sequence.

A time interval processor 154 configured to determine a respective time interval for each pacing sequence of the sequence set. The time interval represents the time from onset of activation of the left ventricle during a cardiac cycle to the time point of closure of the mitral valve for the cardiac cycle as determined by the valve closure processor 152. Hence, the time interval processor 154 determines such a time interval for each of the pacing sequences that are tested by the IMD 100. This means that the heart is paced according to a particular pacing sequence of the sequence set for at least one cardiac cycle. During this at least one cardiac cycle the implantable sensor 60 records the sensor signal and the valve closure processor 152 determines the respective time point(s) of mitral valve closure. The respective onset(s) of LV activity is(are) also determined for the at least one cardiac cycle by the activation detector 151.

A selector 156 of the IMD 100 investigates the time intervals determined by the time interval processor 154 in order to identify and select the pacing sequence that is associated with and resulted in the shortest time interval as determined by the time interval processor 154. Hence, the pacing sequence that minimizes the time from onset of LV activation to the closure of the mitral valve is to be used as optimal pacing sequence for the IMD 100 when applying pacing pulses to the left ventricle with the multipolar LV lead. Information of the pacing sequence selected by the selector 156 is stored in a memory 170 of the IMD 100. This information thereby identifies the pacing sequence as a currently optimal pacing sequence for the subject.

The information stored in the memory 170 is advantageously used by the controller 150 to operate the ventricular pulse generator 130. Hence, the currently optimal pacing sequence is preferably used by the controller 150 to control the ventricular pulse generator 130 to apply pacing pulses to the multiple pacing electrodes of the multipolar LV lead.

In addition, or alternatively, the information stored in the memory 170 with regard to the currently optimal pacing sequence can be transmitted to the non-implantable data processing device 200, see FIG. 1, for instance to be displayed to the subject's physician. The IMD 100 then comprises a transceiver (TX/RX) 190 having communication functionality for transmitting data to and receiving data from the data processing device. The transceiver 190 can be implemented as a single unit having both transmitting functionality and receiving functionality. In an alternative approach, the transceiver is replaced by one or more transmitters and one or more receivers. The transceiver (or transmitter and receiver) is connected to an antenna 195 to affect the communication. The antenna 195 could be an RF antenna or an inductive antenna, as illustrative examples.

In a particular embodiment, the controller 150 is configured to select an initial pacing sequence of the sequence set during the process of identifying the currently optimal pacing sequence. The remaining pacing sequences of the sequence set are then obtained by changing the pacing order at which pacing pulses are applied to the pacing electrodes of the multipolar LV lead relative the pacing order of the initial pacing sequence. Alternatively, or in addition, pacing sequences can be obtained by changing at least one pulse-to-pulse delay of applying pacing pulses at the multiple pacing electrodes of the multipolar LV lead relative the pulse-to-pulse delays of the initial pacing sequence.

Thus, a large number of pacing sequences can be obtained from an initial pacing sequence by changing the pacing order and/or the pulse-to-pulse delays. For instance, if the multipolar LV lead comprises four pacing electrodes, 24 different pacing orders are possible and if the pulse-to-pulse delay can be according to any of, for instance, five different delay values, there are in total 125 different delay combinations with four pacing electrodes. If both pacing order and pulse-to-pulse delays can be changed in this example there will be potentially 3.000 different pacing sequences. In practice it is generally not possible to test all such pacing sequences. Thus, in a particular embodiment, the pacing sequences of the sequence set have the same pacing order but use different pulse-to-pulse delays. Hence, the order at which pacing pulses are applied to different pacing sites by the multipolar LV lead is preferably fixed during an optimization process and for a particular subject, whereas the pulse-to-pulse delays are varied.

The particular pacing order used by the initial pacing sequence and preferably of all other pacing sequences in the sequence set can be defined and stored in the memory 170. Alternatively, the subject's physician determines this pacing order based on the particular heart condition of the subject. Information of the selected pacing order is then downloaded to the IMD 100 through the transceiver 190 and entered in the memory 170.

In an embodiment, the pacing order of the pacing sequences in the sequence set defines an initial pacing at a most proximal pacing electrode 38, see FIG. 1, of the multipolar LV lead 30, followed by pacing at a most distal pacing electrode 32 of the multipolar LV lead 30 and followed by pacing at the N−2 remaining pacing electrode(s) 34, 36 of the multipolar LV lead 30 in a defined order.

The most proximal pacing electrode 38 is preferably positioned at a basal site of the heart and the left ventricle. Such initial basal contraction is believed to promote reduction of the mitral annular diameter early in systole. The early reduction of the size of the mitral annulus increases the area of contact between the two leaflets of the mitral valve, thereby decreasing leakage during the ensuing LV contraction.

The most distal electrode is preferably positioned at or in connection with the apex of the left ventricle. Hence, the pacing order then provides the initial basal pacing followed by pacing at the apex and then continuing up from the apex towards the basal portion of the left ventricle. Hence, a preferred pacing order with reference to FIG. 1 is the basal pacing electrode 38, the apical pacing electrode 32 followed by the pacing electrode 34 and then the pacing electrode 36. This pacing order will enhance the contraction of the left ventricle and contribute to counter clock-wise rotation associated with left ventricular shortening. The initial basal pacing that promotes reduction in mitral annular diameter then occurs prior to the rotation and shortening of the left ventricle and therefore closely mimics the mechanical contraction pattern of a healthy heart.

The present embodiments provide several advantages to cardiac resynchronization therapy (CRT) and heart failure patients equipped with an IMD as disclosed herein. The embodiments reduce the risk of mitral regurgitation in CRT and provide a natural ventricular activation pattern that mimics the normal physiology of the heart.

Thus, the above disclosed preferred pacing order is preferably used for the initial pacing sequence selected by the controller 150 and preferably for the remaining pacing sequences of the sequence set. However, for some subjects other pacing sequences could be more beneficial to the particular heart conditions of these subjects. In such a case, another defined pacing order could then be used for the pacing sequences in the sequence set.

The controller 150 then changes pulse-to-pulse or intraventricular delays between the different pacing sequences so that each pacing sequence of the sequence set preferably has a unique combination of pulse-to-pulse delays although the pacing sequences use the same selected pacing order. The controller 150 could then test different pulse-to-pulse delays in an interval of, for instance, 5 ms to 50 ms and in different steps of, for instance, 5 ms, optionally decreasing the step-size to 1-2 ms close to the optimum. These values, i.e. smallest possible pulse-to-pulse delay, largest possible pulse-to-pulse delay and smallest delay step can be determined by the subject's physician and downloaded to the IMD 100 and the memory 170 using the transceiver 190. Hence, these delay values can be set based on the particular heart condition of the subject.

Figure 5:
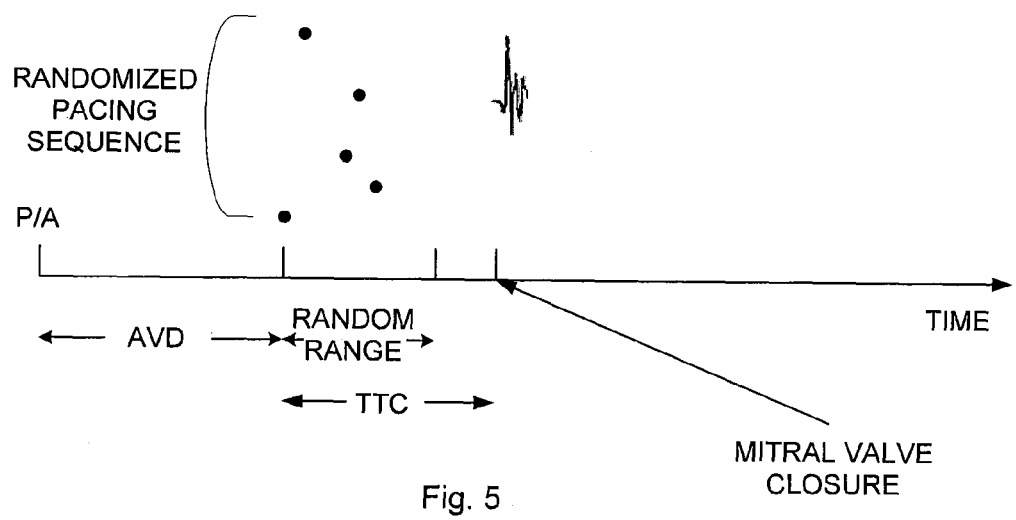
FIG. 5 schematically illustrates the principle of randomizing pacing sequences and the resulting time to closure (TTC) of the mitral valve.

In an embodiment, the controller 150 could test each possible combination of pulse-to-pulse delay. However, such a procedure generally implies that a relative large number of different pacing sequences need to be tested. In an alternative approach, the controller 150 generates remaining pacing sequences of the sequence set from the initial pacing sequence by a randomization procedure. FIG. 5 schematically illustrates this concept. Thus, the controller 150 uses a random range within which different pulse-to-pulse delays can be varied to thereby obtain different randomized pacing sequences. For each such randomized pacing sequence the time from LV activation to closure of the mitral valve (TTC) is determined as disclosed herein. The controller 150 could randomly generate a fixed number of different pacing sequences and then identify the one in the optimization process that resulted in the shortest time interval. This identified pacing sequence could then be used as initial pacing sequence in a subsequent optimization process but then optionally using a smaller random range, i.e. smaller step size. This procedure can then be repeated a number of times until the time intervals do not significantly change any more. Other procedures of selecting an optimal value using a randomization process are possible and within the scope of the embodiments.

In a particular embodiment, the controller 150 causes the ventricular pulse generator 130 to apply pacing pulses according to a particular pacing sequence of the sequence set for multiple cardiac cycles. In such a case, the time interval processor 154 determines a respective time interval from onset of LV activation to the time point of closure of the mitral valve for the different cardiac cycles. The time interval processor 154 furthermore advantageously calculates an average time interval for the particular pacing sequence. The standard deviation may also be calculated for controlling the number of cardiac cycles necessary to measure a reliable time interval. Hence, the same pacing sequence is tested during multiple cardiac cycles until the standard deviation falls below a preconfigured threshold value. Then a new pacing sequence can be tested.

Averaging the time intervals reduce the effects of noise and thereby gives more reliable data when selecting optimal pacing sequence.

Generally, the ventricular filling can have an influence on the time interval from onset of LV activation to the time point of closure of the mitral valve. In an embodiment, the IMD 100 therefore performs the pacing sequence optimization process during stable heart rhythm. Another reason for performing the optimization process during conditions of stable heart rhythm is that some subjects may suffer from heart rate dependent conduction blocks. Thus, the depolarization propagation over the left ventricle for these subjects can differ significantly depending on the whether the current heart rate is above or below the particular heart rate for which the conduction block appears.

The IMD 100 could therefore comprise an intracardiac electrogram (IEGM) processor 160 (see FIG. 2) connected to the connector 110 and configured to generate an IEGM signal based on electrical activity of the heart sensed by at least one sensing (and pacing) electrode connected to the connector 110. The IMD 100 then preferably comprises a heart rate processor 158 configured to process the IEGM signal to determine a current heart rate of the subject's heart. The controller 150 could then be configured to control the ventricular pulse generator 130 to generate pacing pulses to be applied to the multiple electrodes of the multipolar LV lead according to the multiple different pacing sequences if the current heart rate is within a defined heart rate interval, such as below a defined maximum heart rate. This heart rate interval could be determined individually for each subject by the subject's physician. Information of the defined heart rate interval is then preferably downloaded to the IMD 100 and the memory 170 through the transceiver 190.

The optimization parameter used according to the embodiments is the time interval from the onset of LV activation to the time point of closure of the mitral valve for a cardiac cycle or heart beat. Onset of LV activation is in an embodiment defined as onset of contraction of the left ventricle during the cardiac cycle. Hence, in this embodiment the activation detector 151 detects onset of contraction of the left ventricle.

Onset of (mechanical) contraction of the left ventricle can be determined according to various embodiments. In a first embodiment, the implantable sensor 60 can be used not only for generating the sensor signal from which the time point of closure of the mitral valve can be identified. If the implantable sensor 60 is in the form of a microphone or other acoustic sensor it can also be used to identify the onset of LV contraction. In such a case, the implantable sensor 60 is advantageously arranged in the septum between the right ventricle and the left ventricle and with the sensor surface facing into the left ventricle. Onset of LV contraction can then be registered with the implantable sensor 60 at this position.

In an alternative approach, an implantable basal accelerometer can be used to monitor LV contraction, since the AV-plane is accelerated towards the apex during contraction. In individual patients with abnormal motion patterns other sensor sites than a basal position may be more suitable for monitoring. The connector 110 of the IMD 100 then comprises at least one terminal (not illustrated) to also be connectable to the implantable accelerometer (not illustrated) in addition to the optional at least one terminal 118 to be connected to the implantable sensor 60. The accelerometer is then advantageously provided in the septum as discussed above and will record an acceleration signal from which onset of LV contraction can be determined by the time interval processor 154.

In these embodiments, the activation detector 151 receives the signal from the connected sensor through the connector 110 and processes the signal in order to identify the time point of onset of contraction of the left ventricle during a cardiac cycle.

A further variant is to determine the onset of LV contraction through impedance measurements. Thus, a sub-threshold electric signal is generated by the ventricular pulse generator 130 or an optional atrial pulse generator 135 and is applied over two electrodes connected to the IMD 100. This electric signal has a known current profile. The voltage of a resulting electric signal sensed over two electrodes is recorded by the activation detector 151 and used together with the current profile to determine an impedance signal according to well known techniques. Onset of LV contraction can then be identified from the impedance signal.

In an alternative approach a substitute or representation of onset of LV contraction is used by the IMD 100. For instance, there is generally a well-defined relationship between the onset of depolarization of the left ventricle and the onset of contraction of the left ventricle. Hence, in an embodiment, the activation detector 151 is configured to detect the onset of depolarization of the left ventricle. Onset of LV depolarization can be determined from the IEGM signal recorded by the previously discussed IEGM processor 160. Thus, in such a case, the activation detector 151 receives this IEGM signal from the IEGM processor 160. In this case, the IEGM signal could be an estimate of a surface electrocardiogram (ECG). The IEGM processor 160 then performs the electrical measurements over two or more case electrodes provided on the IMD 100 and remotely relative the heart.

Alternatively, onset of LV activation could be defined as the time point of generation and/or application of the first pacing pulse of the pacing sequence. The activation detector 151 does then not necessarily need to perform the detection based on any signal received by the connector 110. In clear contrast, once the ventricular pulse generator 130 generates and applies a first pacing pulse of pacing sequence to one of the pacing electrodes of the multipolar LV lead, the activation detector 151 notifies this event as the onset of LV activation.

In a related approach, onset of LV activation is detected by the activation detector 151 as the point in time of application of the first pacing pulse of a pacing sequence that resulted in capture in the left ventricle, i.e. the start of a depolarization. In such a case, the activation detector 151 could get a notification by a ventricular sensing circuit 140 whether the applied pacing pulses of a pacing sequence lead to capture or not. This information is then used to identify the time point of onset of LV activation.

In an embodiment, the IMD 100 could use a compensation factor when determining the time interval based on LV depolarization depending on whether the LV depolarization is due to an intrinsic activation or a paced activation. Hence, if the LV depolarization is due to an intrinsic activation the time interval processor 154 determines the time interval from onset of LV depolarization to the time point of closure of the mitral valve. However, if the LV depolarization is due to a paced activation the time interval processor 154 instead determines the time interval from onset of LV depolarization to the time point of closure of the mitral valve plus a compensation factor. This compensation factor is generally within the interval from about 20 ms to about 50 ms. The compensation factor can be determined by the subject's physician and downloaded to the IMD 100 and the memory 170 through the transceiver 190. The reason for applying such an optional compensation factor is that the depolarization propagation over the left ventricle may be somewhat different for a paced cardiac cycle as compared to an intrinsic cardiac cycle.

When applying pacing pulses according to the pacing sequences in the sequence set some of the pacing pulses may be delivered to refractory tissue in the left ventricle caused by spontaneous or intrinsic activity. The reason for this may be a completely spontaneous ventricular activity. This can be verified by delaying or inhibiting pacing pulses in the pacing sequence and sense for electrical activity on each pacing electrode of the multipolar LV lead. If such electrical activity is sensed, there is a spontaneous ventricular activity.

Another reason for refractory LV tissue may be due to a depolarization wave started by a pacing pulse at one electrode and propagating over the LV tissue. Thus, the activation of certain myocytes emanates from a depolarization wave started by a previously stimulated pacing electrode in the pacing sequence rather than from the pacing electrode situated in connection with the particular myocytes. A way to verify this situation is to first stimulate at one of the pacing electrodes at an atrioventricular (AV) delay, which is shorter than the time from atrial depolarization to a spontaneous depolarization at respective electrode, and to measure the time to an electrical activation at the other electrodes of the multipolar LV lead. A pacing pulse is then applied to the same pacing electrode of the multipolar LV lead at a shorter or longer AV delay and then the time to electrical activation at the other pacing electrodes is once more measured. Those measured timings which should be essentially equal at both AV delays, if the tissue at respective other pacing electrode is non-refractory, are considered to be due to the stimulation applied to the particular pacing electrode, i.e. those timings are independent on the length of the AV delay but are rather an effect of the pacing pulses of the pacing sequence.

In the process of identifying the currently optimal pacing sequence, the timings mentioned above can be determined and stored in the memory 170. They can then be used when determining the pacing sequences by leaving out those pacing electrodes that are located within refractory tissue that otherwise would have been stimulated according to the pacing sequence. A more elegant way could be to leave out one of the pacing electrodes and measure if there is any difference in the time interval from onset of LV activation to mitral valve closure. If there is no change this pacing electrode could be left out from the pacing sequence. Hence, according to the embodiments, not all pacing electrodes of the multipolar LV lead must necessarily be used in the pacing sequence. Thus, if the multipolar LV lead comprises P pacing electrodes, it is sufficient that the pacing sequence use N pacing electrodes, wherein 3≤N≤P.

Figure 4:
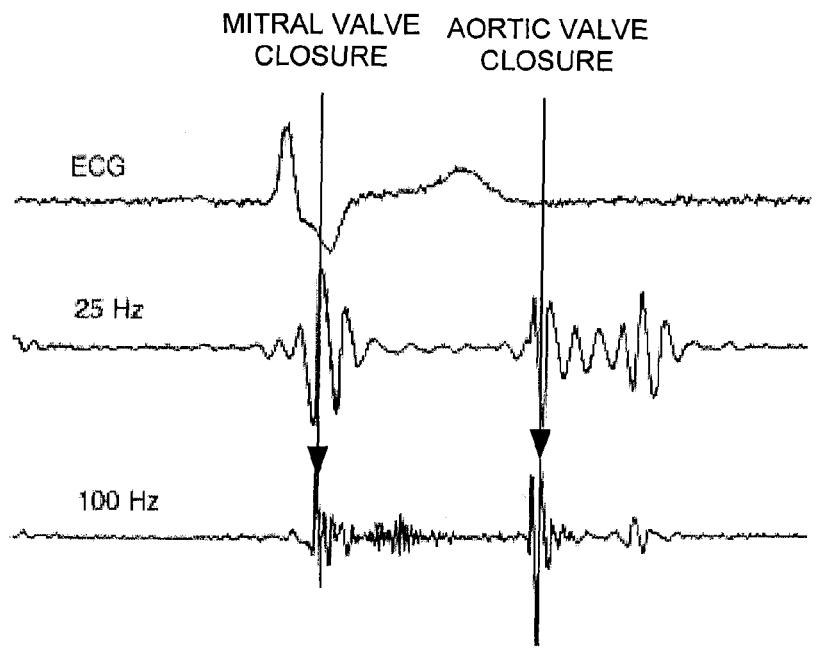
FIG. 4 is a diagram illustrating a phonogram and an electrocardiogram recorded for a human subject during a cardiac cycle.

The implantable sensor 60 used according to the embodiments is advantageously an implantable microphone configured to generate a sensor signal representative of heart sounds from the heart. The valve closure processor 152 is then configured to determine the time point of closure of the mitral valve of the heart to coincide with a time point of heart sound $S_1$ for the cardiac cycle. FIG. 4 illustrates a multi-channel phonocardiogram taken at a paper speed of 100 mm/s. The top channel shows an electrocardiogram (ECG lead II). The second and third channels present data from an implantable microphone placed near the cardiac apex. The cardiovascular sound is filtered so that the second channel records frequencies below 25 Hz and the third channel below 100 Hz. The mitral valve closure is clearly visible from the sensor signal as the first heart sound $S_1$. The figure also shows the second heart sound $S_2$ corresponding to aortic valve closure.

An implantable microphone could be provided on a separate catheter connectable to the connector 110, on one of the connectable implantable medical leads or be provided inside the housing of the IMD 100.

A further variant to detect closure of the mitral valve is to use an accelerometer present in the housing of the IMD 100 to detect vibrations of the housing. Such an implantable sensor is disclosed in U.S. Pat. No. 6,044,299.

In an alternative embodiment, the implantable sensor 60 is an implantable pressure sensor. The pressure sensor 60 is configured to generate a left atrial pressure (LAP) signal representative of the left atrial pressure of the subject.

These embodiments can be used in connection with any implantable sensor that is capable of recording a LAP signal or a signal that is at least representative of the LAP during at least one cardiac cycle. Such implantable sensors are known in the art. For instance, implantable LAP sensors that can be used according to the embodiments are disclosed in U.S. Pat. No. 7,418,868 B1, U.S. Pat. No. 7,515,971 B1 and the international application WO 2005/107583 A2. The LAP sensors disclosed in the above mentioned documents should merely be seen as illustrative examples of implantable pressure sensors that can be used and the embodiments are not limited thereto.

Figure 3:
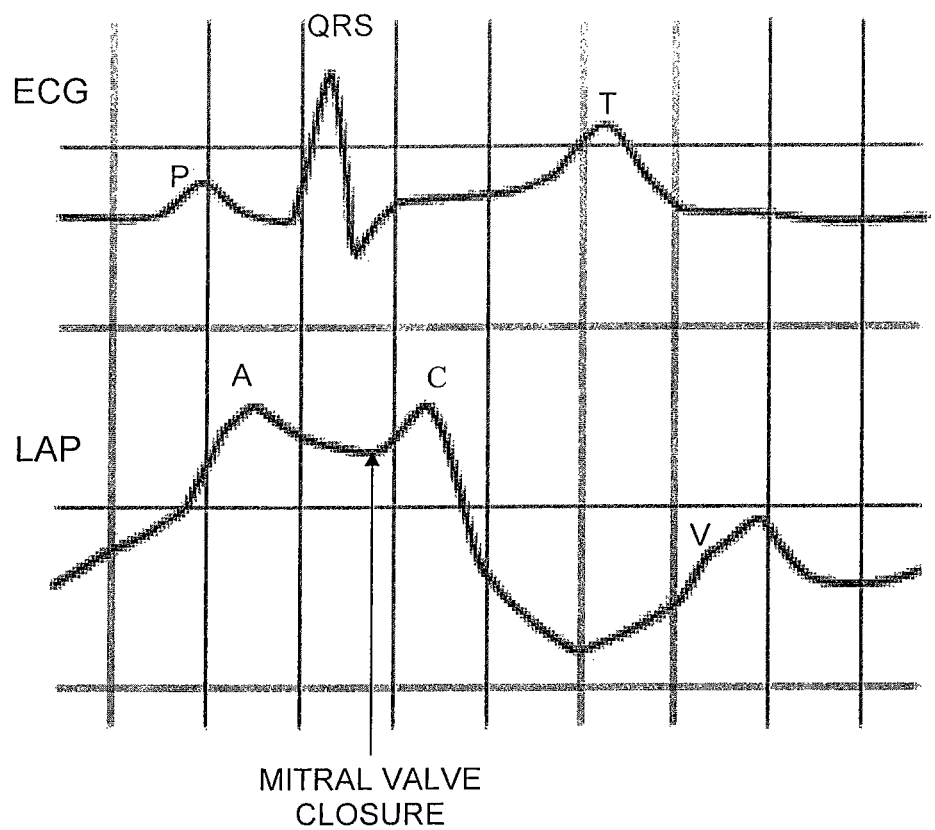
FIG. 3 is a diagram illustrating a left atrial pressure signal and an electrocardiogram recorded for a human subject during a cardiac cycle.

The time interval processor 154 is then configured to process the LAP signal in order to identify a time point of closure of the mitral valve of the heart. The time interval processor 154 identifies the mitral valve closure as coinciding in time immediately after the A-wave in the LAP signal for a cardiac cycle and in connection to the C-wave (if present). This is schematically illustrated in FIG. 3, where the LAP signal is recorded for a cardiac cycle and a corresponding ECG is shown in for the cardiac cycle. FIG. 3 also indicates the C-wave and the V-wave of the LAP signal and the characteristics in the ECG, i.e. P wave, QRS complex and T wave, are indicated.

The IMD 100 of FIG. 2 may, in addition to the determination of the currently optimal pacing sequence for the left ventricle, also determine the optimal AV delay. In such a case, the connector 110 comprises at least one terminal 111 configured to be connected to at least one atrial electrode, preferably provided on an atrial lead. The IMD 100 comprises an atrial pulse generator 135 that is connected to the connector 110 and configured to generate pacing pulses to be applied to the at least one atrial electrode to achieve atrial stimulation. The IMD 100 preferably also comprises an atrial sensing circuit 145 configured to sense electrical activity in an atrium using an atrial electrode connected to the connector 110. A ventricular sensing circuit 140 is likewise implemented in the IMD 100 to sense electrical activity in a ventricle using a ventricular electrode connected to the connector 110.

Optimal AV delay defines an optimal time period from an intrinsic atrial electrical activity as sensed by the atrial sensing circuit 145 or from a paced atrial activity as generated by the atrial pulse generator 135 until a first pacing pulse of the pacing sequence is to be applied by the ventricular pulse generator 130.

Determining optimal AV delays are well known in the art and can be based on various optimization criteria, such as mentioned in the background section. However, the currently optimal pacing sequence to be used for the multipolar LV lead is typically dependent on the particular AV delay used by the controller 150 for coordinating ventricular pacing relative atrial (intrinsic or paced) activity. Hence, in an embodiment, the IMD 100 first optimizes the AV delay by testing various such AV delays and recording a respective parameter value for a selected hemodynamic parameter according to prior art techniques. The AV delay that leads to most optimal hemodynamic performance as determined from the recorded parameter values is then used by the controller 150 and entered in the memory 170. This optimal AV delay value is then used when the IMD 100 is about to test and select optimal pacing sequence for the multipolar LV lead. Hence, the same optimal AV delay is preferably used throughout the optimization process.

FIG. 5 schematically illustrates an optimal AV delay (AVD) from a paced (P-wave) or an intrinsic (A-wave) atrial activity.

If the IMD 100 later on is about to check whether an updated optimization process should be initiated for the AV delay, the previously determined optimal pacing sequence could be used throughout the updated AV delay optimization procedure. Once an updated optimal AV delay is obtained an updated optimization process for the selection of the optimal pacing sequence can be initiated while using the updated optimal AV delay during the optimization process.

The initiation or trigger to start an optimization process by the IMD 100 can be performed according to various embodiments. In an embodiment, the optimization process is initiated based on the reception of a trigger signal by the transceiver 190. In such a case, the trigger signal is typically generated by and transmitted from the data processing device (FIG. 1) when the subject is visiting his/her physician. As a further alternative, the trigger signal could be generated at home with a data processing device in the form of a home monitoring device. The received trigger signal then causes the controller 150 to initiate the optimization process as disclosed herein.

In an alternative, or additional, approach, the IMD 100 could be configured to perform an optimization process at predefined time intervals. For instance, the IMD 100 could be configured to perform a new optimization process once every month, once every half year, etc. The periodicity or time instances at which a new optimization process is to be started are typically set by the subject's physician and programmed into the IMD 100 and information thereof is stored in the memory 170.

A further embodiment that can be used separately or in combination of any of the embodiments disclosed above is to let the IMD 100 determine when a new optimization process is needed. In such a case, the IMD 100 could be configured to, periodically or at defined time instances, determine the time interval from onset of activation of the left ventricle to the time point of closure of the mitral valve for a cardiac cycle. Hence, the valve closure processor 152 and the time interval processor 154 are then configured to determine this time interval. The controller 150 then compares the determined time interval and if it exceeds a predefined threshold value, the controller 150 triggers a new optimization process. Thus, in this case the IMD 100 monitors whether the selected pacing sequence still achieves acceptable time intervals from onset of activation of the left ventricle to the time point of closure of the mitral valve. If the pacing sequence would result in a too long time interval, i.e. the determined time interval exceeds the threshold value, then a new optimization process should be started for possibly finding a more appropriate pacing sequence.

As illustrated in FIG. 2, the IMD 100 and the connector 110 may also be connected to a right ventricular lead. Hence, the connector 110 then comprises terminals 112, 113 to be electrically connected to pacing electrodes, such as tip electrode and ring electrode of the right ventricular lead. The connector 110 may optionally also comprise a terminal 119 to be connected to a so-called case electrode. Such a case electrode can be the housing or part of the housing of the IMD 100 and can act as return electrode for unipolar leads.

The ventricular and atrial pulse generators 130, 135 of the IMD 100 may include dedicated, independent pulse generators, multiplexed pulse generators, or shared pulse generators. The pulse generators 130, 135 are controlled by the controller 150 via appropriate control signals, respectively, to trigger or inhibit the stimulating pulses.

The ventricular and atrial sensing circuits 140, 145 of the IMD 100 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 140, 145 preferably employs one or more low power, precision amplifiers with programmable gain and/or automatic gain control, band-pass filtering, and a threshold detection circuit, as known in the art, to selectively sense the cardiac signal of interest.

The outputs of the ventricular and atrial sensing circuits 140, 145 are connected to the controller 150, which, in turn, is able to trigger or inhibit the ventricular and atrial pulse generators 130, 135, respectively, in a demand fashion in response to the absence or presence of cardiac activity in the appropriate chambers of the heart.

The controller 150 of the IMD 100 is preferably in the form of a programmable microcontroller 150 that controls the operation of the IMD 100. The controller 150 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 150 is configured to process or monitor input signals as controlled by a program code stored in a designated memory block. The type of controller 150 is not critical to the described implementations. In clear contrast, any suitable controller may be used that carries out the functions described herein. The use of microprocessor-based control circuits for performing timing and data analysis functions are well known in the art.

Furthermore, the controller 150 is also typically capable of analyzing information output from the sensing circuits 140, 145 to determine or detect whether and to what degree tissue capture has occurred and to program a pulse, or pulse sequence, in response to such determinations. The sensing circuits 140, 145, in turn, receive control signals over signal lines from the controller 150 for purposes of controlling the gain, threshold, polarization charge removal circuitry, and the timing of any blocking circuitry coupled to the inputs of the sensing circuits 140, 145 as is known in the art.

The optional electronic configuration switch 120 includes a plurality of switches for connecting the desired connector terminals 111-119 to the appropriate I/O circuits, thereby providing complete electrode programmability. Accordingly, the electronic configuration switch 120, in response to a control signal from the controller 150, determines the polarity of the stimulating pulses by selectively closing the appropriate combination of switches (not shown) as is known in the art.

While a particular multi-chamber device is shown in FIG. 2, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination.

The IMD 100 additionally includes a battery 180 that provides operating power to all of the circuits shown in FIG. 2.

In FIG. 2, the valve closure processor 152, the time interval processor 154, the selector 156 and the optional heart rate processor 158 have been illustrated as being run by the controller 150. These units 150-158 can then be implemented as a computer program product stored in the memory 170 and loaded and run on a general purpose or specially adapted computer, processor or microprocessor, represented by the controller 150 in FIG. 2. The software includes computer program code elements or software code portions effectuating the operation of the units 152-158. The program may be stored in whole or part, on or in one or more suitable computer readable media or data storage means that can be provided in an IMD 100.

In an alternative approach, the units 152-158 are implemented as hardware circuits in the IMD 100, preferably connected to the controller 150.

Figure 6:
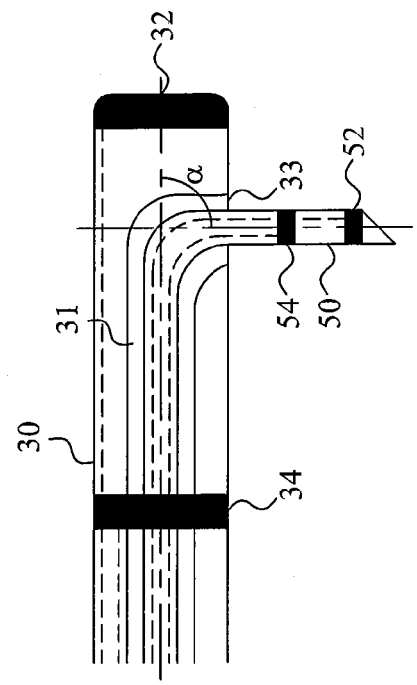
FIG. 6 is a partly cross-sectional view of a distal portion of a multipolar left ventricular lead according to an embodiment.

It is not unlikely that the subject may suffer from subendocardial conduction blocks due to ischemia or fibrosis. In such a case, the multipolar LV lead of the embodiments can comprise both endocardial pacing electrodes and epicardial pacing electrodes. The distal end of such a multipolar LV lead is shown in FIG. 6.

The multipolar LV lead 30 comprises a lumen 31 that houses a myocardium penetrating catheter 50 that is movable within the lumen 31 and relative the multipolar LV lead 30.

The myocardium penetrating catheter 50 comprises at least one endocardial electrode 52, 54. The at least one endocardial electrode 52, 54 is electrically connected, through a respective electrical conductor, to a respective electrode terminal provided in connection with the proximal end of the multipolar LV lead 30. The endocardial electrode 52, 54 of the myocardium penetrating catheter 50 is configured to be positioned in the myocardium, i.e. in a sub-endocardial site, and is thereby interposed between the endocardium and the epicardium.

The myocardium penetrating catheter 50 is designed to be moved inside the lumen 31 and extend beyond the outer surface (lateral/envelope surface) of the multipolar LV lead 30. The distal end of the myocardium penetrating catheter 50 is sharpened or needle-like in order to be able to penetrate through the myocardium to thereby move the distal end of the myocardium penetrating catheter 50 and thereby the at least one endocardial electrode 52, 54 to a sub-endocardial site and thereby reach endocardial fibers. However, the myocardium penetrating catheter 50 is preferably not moved that far so that it penetrates into the left ventricular cavity. There is a clear sensation to the physician when the myocardium penetrating catheter 50 has pierced through the myocardium and reaches the endocardial fibers. That tissue provides more resistance than the intramural myocardium and the sensation is sufficient to not advance the myocardium penetrating catheter 50 too far to risk penetration into the left ventricular cavity.

The lumen 31 of the multipolar LV lead 30 is preferably turned at its distal end so that the myocardium penetrating catheter 50 can protrude out from the multipolar LV lead 30 on its lateral or envelope surface as indicated in FIG. 6. The turn of the lumen 31 could be close to 90° as shown in FIG. 6, which causes the myocardium penetrating catheter 50 to protrude at least close to perpendicular to the main axis of the multipolar LV lead 30. The embodiments are, however, not limited thereto. In clear contrast, the turn of the lumen 31 can be designed in any other angle larger than 0° and smaller than 180°. It is generally preferred if the angle α between the main axis of the protruding part of the myocardium penetrating catheter 50 and the main axis of the multipolar LV lead 30 is in the interval $0°<\alpha\leq 90°$, preferably $40°\leq\alpha\leq 60°$, such as about 50°.

The lumen 31 can end in an opening 33 in the lateral surface of the multipolar LV lead 30. The myocardium penetrating catheter 50 is then moved partly out from the lumen 31 through the opening 33. In an alternative approach the lumen 31 does not have any opening but instead ends at the outer insulating tubing of the multipolar LV lead 30 or is provided with a dedicated cover. The lumen 31 is then initially closed. However, as the myocardium penetrating catheter 50 is moved through the lumen 31, for instance by pushing at the proximal end of the myocardium penetrating catheter 50, the myocardium penetrating catheter 50 will penetrate through the outer insulating tubing or the cover to thereby protrude and extend beyond the lateral surface of the multipolar LV lead 30.

In a particular embodiment, the multipolar LV lead 30 comprises N pacing electrodes 32, 34, 36, 38, 52, 54 (see FIG. 7) in total. In such a case, M pacing electrodes 52, 54 of these N pacing electrodes 32, 34, 36, 38, 52, 54 are endocardial pacing electrodes 52, 54 positioned on the myocardium penetrating catheter 50. The remaining N−M pacing electrodes 32, 34, 36, 38 are epicardial pacing electrodes 32, 34, 36, 38. In such a case, M is an integer equal to or larger than one and M<N.

Figure 7:
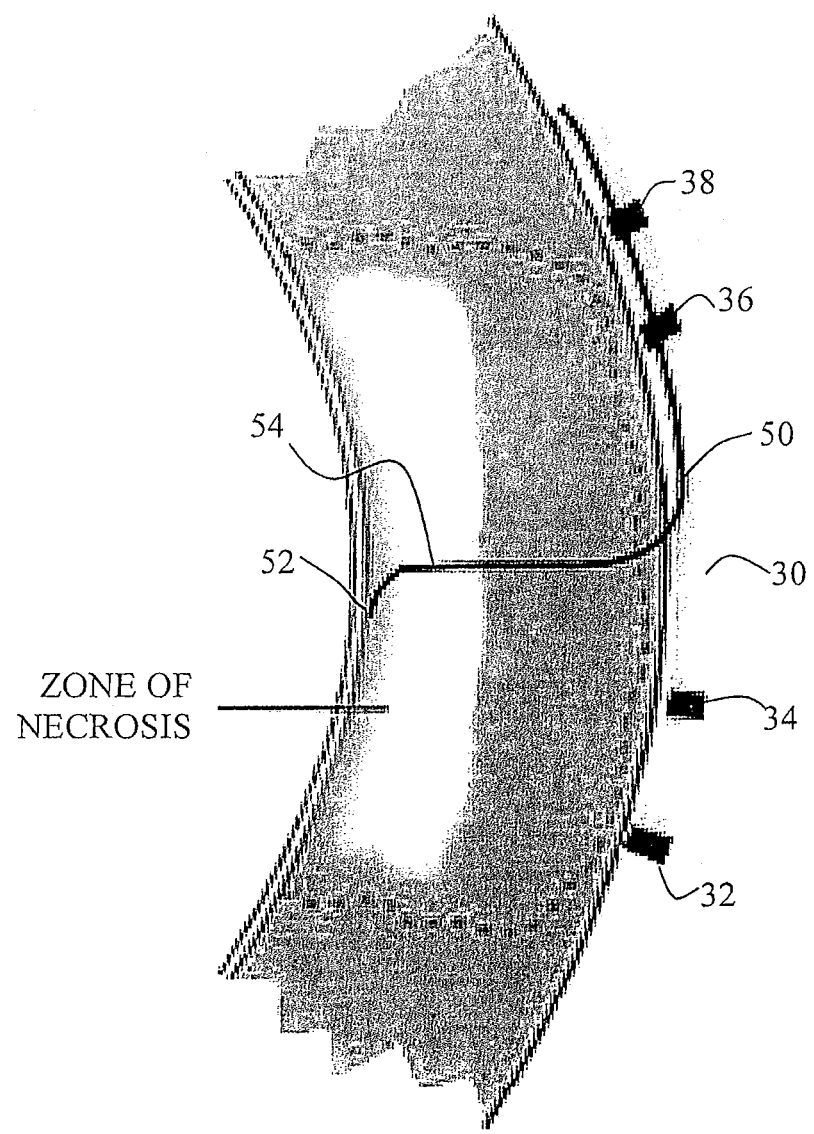
FIG. 7 schematically illustrates the concept of having endocardial and epicardial pacing electrodes at a multipolar left ventricular lead according to an embodiment.

The at least one endocardial electrode 52, 54 can then be used to provide endocardial or intramural pacing, which is advantageous in the case there is a zone of ischemic or necrotic tissue in the myocardium as indicated in FIG. 7.

In a particular embodiment, the IMD 100 uses a same pacing order for all pacing sequences in the sequence set. This pacing order could then be adapted for use in connection with a multipolar LV lead 30 having a myocardium penetrating catheter 50 with at least one endocardial electrode 52, 54. This pacing order could then be an initial pacing at a most proximal electrode 38 of the epicardial pacing electrodes 32, 34, 36, 38, followed by pacing at at least one of the endocardial pacing electrodes 52, 54 followed by pacing at the remaining epicardial pacing electrodes 32, 34, 36 in a defined order, preferably from an apical site of the left ventricle up towards the basal portion of the left ventricle.

Figure 8:
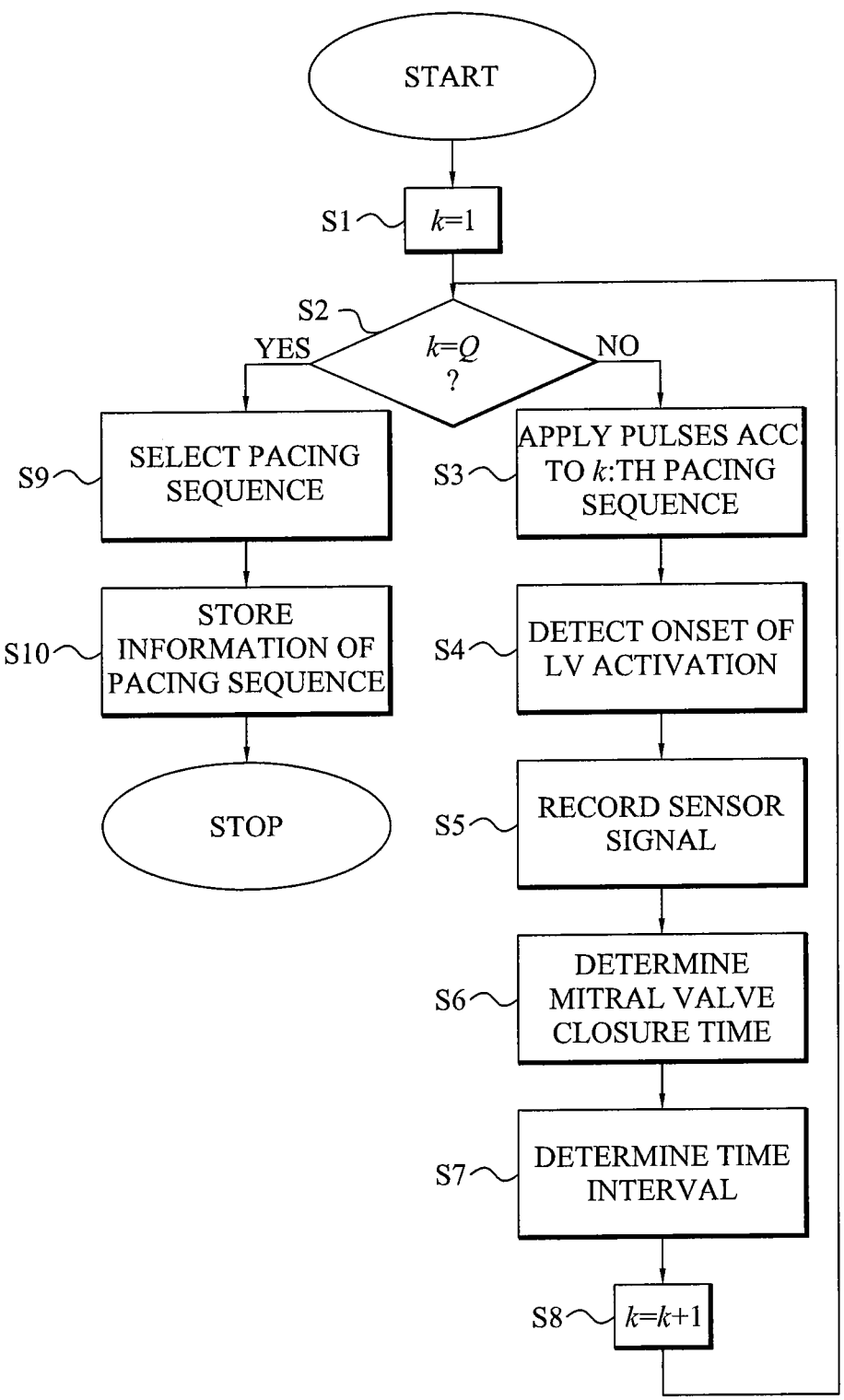
FIG. 8 is flow diagram illustrating a method of selecting pacing sequence for an implantable medical device according to an embodiment.

FIG. 8 is a flow diagram illustrating a method of selecting pacing sequence for an IMD according to an embodiment. In the method a sequence counter k is used in order to verify whether all pacing sequences in the sequence set have been tested. In this particular example, the parameter Q denotes the total number of such pacing sequences in the sequence set. Thus, in a first optional step S1 the sequence counter is set to one, i.e. k=1. A next optional step S2 checks whether k=Q, i.e. whether all pacing sequences of the sequence set have been tested. Since k=1<Q the method continues to step S3. Step S3 applies pacing pulses to the multiple pacing electrodes of the multipolar LV lead according to the $k^{th}$ acing sequence of the sequence set. A next step S4 detects onset of LV activation for the cardiac cycle. The following step S5 records a sensor signal for the heart by the implantable sensor. This sensor signal is processed in step S6 to determine a time point of closure of the mitral valve of the heart for the cardiac cycle during which pacing pulses are applied according to the $k^{th}$ pacing sequence in step S3. A next step S7 determines a time interval from onset of LV activation to the time point of closure of the mitral valve for the cardiac cycle and for the $k^{th}$ pacing sequence. The sequence counter k is then increased by one and the method returns to step S2. Hence, steps S3 to S7 are repeated for each pacing sequence in the sequence set to thereby determine a respective time interval obtained by pacing the heart according to the particular pacing sequence.

Once all pacing sequences in the set have been tested, i.e. k=Q in step S2, the method continues to step S9. This step S9 selects the pacing sequence of the sequence set that is associated with and resulted in the shortest time interval as determined in step S7. Information of this selected pacing sequence is then stored in a memory of the IMD in step S10 and identifying the selected pacing sequence as the currently optimal pacing sequence for the subject.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical device comprising:
    a connector connectable to a multipolar left ventricular lead comprising N pacing electrodes configured to be arranged at multiple respective sites in connection with a left ventricle of a heart in a subject, wherein N is an integer equal to or larger than three;
    a valve closure processor configured to determine a time point of closure of the mitral valve of said heart for a cardiac cycle based on a sensor signal recorded for said heart by an implantable sensor comprised in said implantable medical device or connectable to said connector;

a ventricular pulse generator connected to said connector and configured to generate pacing pulses to be applied to said N pacing electrodes;

a pulse generator controller connected to said ventricular pulse generator and configured to control said ventricular pulse generator to generate pacing pulses to be applied to said N pacing electrodes according to multiple different pacing sequences of a sequence set, wherein each pacing sequence of said sequence set defines a pacing order at which pacing pulses are applied to said N pacing electrodes and pulse-to-pulse delays of applying said pacing pulses at said N pacing electrodes according to said pacing order;

an activation detector configured to detect onset of activation of said left ventricle for a cardiac cycle;

a time interval processor configured to determine, for each pacing sequence of said sequence set, a time interval from said onset of activation of said left ventricle detected by said activation detector to said time point of closure of said mitral valve for said cardiac cycle as determined by said valve closure processor;

a selector configured to select the pacing sequence of said sequence set that is associated with the shortest time interval as determined by said time interval processor; and a memory configured to store information of said pacing sequence selected by said selector, said information identifying said pacing sequence as a currently optimal pacing sequence for said subject;

wherein said multipolar left ventricular lead comprises a lumen housing a myocardium penetrating catheter with M endocardial pacing electrodes and remaining N−M pacing electrodes of said multipolar left ventricular lead are epicardial pacing electrodes, wherein M is an integer equal to or larger than one and M<N.

2. The implantable medical device according to claim 1, wherein said pulse generator controller is configured to select an initial pacing sequence of said sequence set and generate remaining pacing sequences of said sequence set by changing a pacing order at which pacing pulses are applied to said N pacing electrodes relative a pacing order of said initial pacing sequence and/or by changing at least one pulse-to-pulse delay of applying said pacing pulses at said N pacing electrodes relative the pulse-to-pulse delays of said initial pacing sequence.

3. The implantable medical device according to claim 1, wherein said pulse generator controller is configured to select said multiple different pacing sequences of said sequence set having a same pacing order at which pacing pulses are applied to said N pacing electrodes (but having different combinations of pulse-to-pulse delays.

4. The implantable medical device according to claim 3, wherein said pulse generator controller is configured to select said same pacing order defining an initial pacing at a most proximal pacing electrode of said N pacing electrodes, said most proximal pacing electrode is configured to be positioned at a basal site of said heart, followed by pacing at a most distal pacing electrode of said N pacing electrodes, said most distal electrode is configured to be positioned at an apex of said left ventricle, followed by pacing at N−2 remaining pacing electrode(s) of said N pacing electrodes in a defined order.

5. The implantable medical device according to claim 1, further comprising:

an intracardiac electrogram processor connected to said connector and configured to generate an intracardiac electrogram signal based on electric activity of said heart sensed by at least one pacing electrode connectable to said connector; and a heart rate processor configured to process said intracardiac electrogram signal to determine a current heart rate for said heart, wherein said pulse generator controller is configured to control said ventricular pulse generator to generate pacing pulses to be applied to said N pacing electrodes according to said multiple different pacing sequences of said sequence set if said current heart rate is within a defined heart rate interval.

6. The implantable medical device according to claim 1, wherein said activation detector is configured to detect onset of contraction of said left ventricle for said cardiac cycle based on i) a signal received by said connector for a connectable sensor or ii) an impedance signal determined by said activity detector based on an electric signal received by said connector from a connectable pacing electrode.

7. The implantable medical device according to claim 1, wherein said activation detector is configured to detect onset of depolarization of said left ventricle for said cardiac cycle based on an electric signal received by said connector from a connectable pacing electrode.

8. The implantable medical device according to claim 7, wherein said time interval processor is configured to determine, for each pacing sequence of said sequence set, said time interval from onset of depolarization of said left ventricle detected by said activation detector to said time point of closure of said mitral valve for said cardiac cycle as determined by said valve closure processor if said depolarization of said left ventricle is due to an intrinsic activation and determine for each pacing sequence of said sequence set, said time interval from onset of depolarization of said left ventricle detected by said activation detector to said time point of closure of said mitral valve for said cardiac cycle as determined by said valve closure processor plus a compensation factor if said depolarization of said left ventricle is due to a paced activation.

9. The implantable medical device according to claim 1, wherein said activation detector is configured to detect onset of activation of said left ventricle as a time point of application of a first pacing pulse of said respective pacing sequence.

10. The implantable medical device according to claim 1, wherein said implantable sensor is an implantable microphone configured to generate a sensor signal representative of heart sounds from said heart; and said valve closure processor is configured to determine, based on said sensor signal, said time point of closure of said mitral valve of said heart to coincide with a time point of heart sound $S_1$ for said cardiac cycle.

11. The implantable medical device according to claim 1, wherein said pulse generator controller is configured to select said multiple different pacing sequences of said sequence set having a same pacing order at which pacing pulses are applied to said N pacing electrodes but having different pulse-to-pulse delays, said same pacing order defines initial pacing at a most proximal pacing electrode of said N−M epicardial pacing electrodes, said most proximal pacing electrode is configured to be positioned at a basal site of said heart, followed by pacing at said M endocardial pacing electrodes, followed by pacing at N−M−1 remaining epicardial pacing electrode(s) in a defined order.

12. A method of selecting pacing sequence for an implantable medical device, said method comprising:

applying pacing pulses to N pacing electrodes of a multipolar left ventricular lead according to multiple different pacing sequences of a sequence set, wherein said N pacing electrodes are arranged at multiple respective sites in connection with a left ventricle of a heart in a subject, N is an integer equal to or larger than three and each pacing sequence of said sequence set defines a pacing order at which pacing pulses are applied to said N pacing electrodes and pulse-to-pulse delays of applying said pacing pulses to said N pacing electrodes according to said pacing order;

detecting, onset of activation of said left ventricle for a cardiac cycle;

determining, for each pacing sequence of said sequence set and based on a sensor signal recorded for said heart by an implantable sensor, a time point of closure of the mitral valve of said heart for a cardiac cycle during which said heart is paced according to said pacing sequence;

determining, for each pacing sequence of said sequence set, a time interval from said onset of activation of said left ventricle to said time point of closure of said mitral valve for a cardiac cycle;

selecting the pacing sequence of said sequence set that is associated with the shortest time interval; and storing, in a memory, information of said selected pacing sequence, said information identifying said pacing sequence as a currently optimal pacing sequence for said subject.

13. An implantable medical device comprising:

a multipolar left ventricular lead comprising N pacing electrodes, wherein N is an integer equal to or larger than three;

a sensor adapted to detect closure of a mitral valve of a heart;

a valve closure processor configured to detect closure of a mitral valve of a heart based on a sensor signal recorded for said heart by an implantable sensor;

a ventricular pulse generator coupled to said lead and configured to generate pacing pulses to be applied to said N pacing electrodes in accordance with a plurality of pacing sequences;

an activation detector configured to detect onset of activation of a left ventricle in response to said N pacing pulses;

a time interval processor configured to determine a time interval from said onset of activation of said left ventricle detected by said activation detector to closure of said mitral valve; and a selector configured to select the pacing sequence that is associated with the shortest time interval as determined by said time interval processor;

wherein said multipolar left ventricular lead comprises a lumen housing a myocardium penetrating catheter with M endocardial pacing electrodes and remaining N−M pacing electrodes of said multipolar left ventricular lead are epicardial pacing electrodes, wherein M is an integer equal to or larger than one and M<N.

14. The implantable device according to claim 13 further comprising a memory configured to store information of said pacing sequence selected by said selector, said information identifying said pacing sequence as a currently optimal pacing sequence for said subject.

15. The implantable medical device according to claim 13, wherein said sensor is an implantable microphone configured to generate a sensor signal representative of heart sounds from said heart; and said valve closure processor is configured to determine, based on said sensor signal, said time point of closure of said mitral valve of said heart to coincide with a time point of heart sound $S_1$ for said cardiac cycle.

* * * * *